US009811636B2

(12) United States Patent
Dykes et al.

(10) Patent No.: US 9,811,636 B2
(45) Date of Patent: *Nov. 7, 2017

(54) CONNECTED HEALTH CARE SYSTEM

(71) Applicant: BEAM TECHNOLOGIES, Columbus, OH (US)

(72) Inventors: Daniel E Dykes, Columbus, OH (US); Alexander D Curry, Columbus, OH (US); Alex X Frommeyer, Columbus, OH (US)

(73) Assignee: BEAM IP LAB LLC, Columbus, OH (US)

( * ) Notice: Subject to any disclaimer, the term of this patent is extended or adjusted under 35 U.S.C. 154(b) by 579 days.

This patent is subject to a terminal disclaimer.

(21) Appl. No.: 14/492,016

(22) Filed: Sep. 20, 2014

(65) Prior Publication Data
US 2015/0088538 A1 Mar. 26, 2015

Related U.S. Application Data

(60) Provisional application No. 61/880,192, filed on Sep. 20, 2013.

(51) Int. Cl.
G01N 9/30 (2006.01)
G01N 1/10 (2006.01)
(Continued)

(52) U.S. Cl.
CPC ........ G06F 19/345 (2013.01); A46B 15/0004 (2013.01); A46B 15/0012 (2013.01);
(Continued)

(58) Field of Classification Search
CPC ............... G06F 19/345; G06F 19/3418; A46B 15/0004; A46B 15/0014; A46B 15/0071;
(Continued)

(56) References Cited

U.S. PATENT DOCUMENTS

2004/0181346 A1* 9/2004 Sunshine ............... B82Y 15/00
702/22
2006/0141431 A1* 6/2006 Lee ......................... A63F 13/12
434/236

(Continued)

Primary Examiner — Eliza Lam
(74) Attorney, Agent, or Firm — Vorys, Sater, Seymour & Pease LLP

(57) ABSTRACT

A connected health care system is provided with various devices for tracking and monitoring health statistics and behaviors including oral health, fitness, heart health, bone health, salivary diagnostics, diabetes, and further options that will be explored in the subsequent sections. The connected health care system is comprised of various devices, a data transfer medium (i.e. "smartphone"), and the Cloud, which allows for data transfer between multiple platforms and devices. Some devices comprised in the connected health care system include a toothbrush, a connected surface with sensors, a salivary diagnostic system, a breath analysis system, and further devices that will be explored in the subsequent sections. The connected health care system further provides a user identification system utilizing capacitive coupling of the human body between devices.

20 Claims, 5 Drawing Sheets

(51) Int. Cl.
- G06F 19/00 (2011.01)
- G06Q 50/22 (2012.01)
- A61B 5/00 (2006.01)
- A61B 5/1455 (2006.01)
- A61C 19/04 (2006.01)
- A61B 5/0205 (2006.01)
- A61B 5/08 (2006.01)
- A46B 15/00 (2006.01)
- A61C 17/06 (2006.01)
- A61C 17/26 (2006.01)
- A61C 17/22 (2006.01)
- A46B 5/00 (2006.01)

(52) U.S. Cl.
CPC ...... *A46B 15/0014* (2013.01); *A46B 15/0071* (2013.01); *A61B 5/0022* (2013.01); *A61B 5/02055* (2013.01); *A61B 5/082* (2013.01); *A61B 5/14552* (2013.01); *A61B 5/6898* (2013.01); *A61C 17/04* (2013.01); *A61C 17/046* (2013.01); *A61C 17/26* (2013.01); *A61C 19/04* (2013.01); *G06F 19/3418* (2013.01); *G06Q 50/22* (2013.01); *A46B 5/0095* (2013.01); *A46B 2200/1066* (2013.01); *A61B 5/6886* (2013.01); *A61C 17/224* (2013.01)

(58) Field of Classification Search
CPC ... A46B 15/0012; A61C 17/046; A61C 17/04; A61C 17/26; A61C 19/04; A61B 5/082; A61B 5/6898; A61B 5/02055; A61B 5/14552
USPC .......................................................... 705/2–3
See application file for complete search history.

(56) References Cited

U.S. PATENT DOCUMENTS

| | | | |
|---|---|---|---|
| 2009/0291422 A1* | 11/2009 | Puurunen | A46B 15/0006 434/263 |
| 2011/0022025 A1* | 1/2011 | Savoie | A61M 5/14248 604/500 |
| 2012/0295216 A1* | 11/2012 | Dykes | A61C 19/04 433/27 |
| 2013/0032413 A1* | 2/2013 | Smith | 177/1 |
| 2013/0211208 A1* | 8/2013 | Varadan | A61B 5/14552 600/301 |

* cited by examiner

COLLECTION SYSTEM

FILTER SYSTEM

EVALUATION SYSTEM

REPORTING SYSTEM

CONNECTED HEALTH CARE SYSTEM

CROSS-REFERENCE TO RELATED APPLICATIONS

This application claims priority to U.S. Provisional Application No. 61/880,192 filed on Sep. 20, 2013.

BACKGROUND

The subject embodiments relate to the tracking and monitoring of health statistics and behaviors, particularly relating to various devices for tracking and monitoring health statistics and behaviors. In particular, the embodiments relate to a connected health care system that allows for data transfer between multiple platforms and devices.

Dental plaque is a biofilm that forms naturally on teeth between brushing and dental visits. Dental plaque can be a precursor to more severe oral health problems including: dental caries, tooth decay, gingivitis, and chronic periodontitis. The occurrence of dental caries is one of the largest health epidemics in the world and is the most common chronic childhood disease in the United States. Likewise, gingivitis and dental calculus are two of the most common systemic diseases of the body. It is desirable to more effectively remove dental plaque early stage as a preventive measure against more serious disease states. The most common preventive measure implemented to control the formation of dental plaque is the toothbrush.

Additionally, a person spends a significant amount of time each day just preparing for the day. Currently, this time provides little advantage beyond hygiene and cosmetic purposes. Often, a person spends much of this time positioned standing in front of a bathroom sink or other item such that an opportunity to measure health statistics is provided since the user is standing still for an amount of time. Current methods for collecting health statistics as part of the daily routine are largely nonexistent or require the user to deliberately step on a scale to obtain weight and possible body fat percentage.

Further, current diagnostic methods include blood analysis, biopsy, and other large scale tests, which all cause considerable discomfort to the patient. Blood analysis requires the drawing of blood with the use of a hypodermic needle. Biopsy requires the removal of tissue from the suspected affected area. Current diagnostic methods also require significant amounts of time to obtain results with some tests taking multiple days or even weeks to complete. Often, this requires a patient to visit a doctor's office for the initial sample collection and again to obtain the results. Collection of samples often requires the expertise of a medical practitioner, which is costly. Evaluation of samples is often completed in a sophisticated laboratory, which is also very costly.

Consequently, medical practitioners and patients are in need of an adequate health care system for tracking and monitoring health statistics and behaviors. Moreover, medical practitioners and patients are in need of a quicker method of diagnosing diseases, disorders, and conditions. Further, current methods are limiting in both the health statistics that are measured and the passive nature of data collection. Consequently, a connected health care system with various devices for tracking and monitoring health statistics and behaviors is desirable for medical practitioners, patients, and the health care industry.

SUMMARY OF EMBODIMENTS

The embodiments described herein meet the objectives stated in the previous section, and provide a connected health care system for tracking and monitoring health statistics and behaviors. Some health statistics and behaviors include, for example, oral health, fitness, heart health, bone health, salivary diagnostics, diabetes, and other statistics and behaviors. Health statistics and behaviors are tracked and monitored by various devices including, for example, toothbrush, connected surface with sensors, salivary diagnostic system, breath analysis system, and other devices. Further, the connected health care system is comprised of a data transfer medium and the Cloud, which allows for data transfer between multiple platforms and devices. Furthermore, the connected health care system further provides a user identification system utilizing capacitive coupling of the human body between devices.

Accordingly several advantages are to provide a connected health care system with various devices for tracking and monitoring health statistics and behaviors; to provide tracking and monitoring of oral health, fitness, heart health, bone health, salivary diagnostics, diabetes and further options; to provide a system for data transfer between multiple platforms and devices; and to provide for user identification utilizing capacitive coupling of the human body between devices. Still further advantages will become apparent from a study of the following descriptions and accompanying drawings.

BRIEF DESCRIPTION OF THE DRAWINGS

The drawings and embodiments described herein are illustrative of multiple alternative structures, aspects, and features of the embodiments described and claimed herein, and they are not be understood as limiting the scope of the embodiments. It will be further understood that the drawing figures described and provided herein are not to scale, and that the embodiments are not limited to the precise arrangements and instrumentalities shown.

MULTIPLE EMBODIMENTS AND ALTERNATIVES

According to multiple embodiments and alternatives herein, a connected health care system and applications thereof shall be discussed in the present section.

A plurality of embodiments comprises a connected health care system that allows a plurality of health devices to transfer data wirelessly between said health devices, a data transfer medium, and the Cloud.

Figure 1:
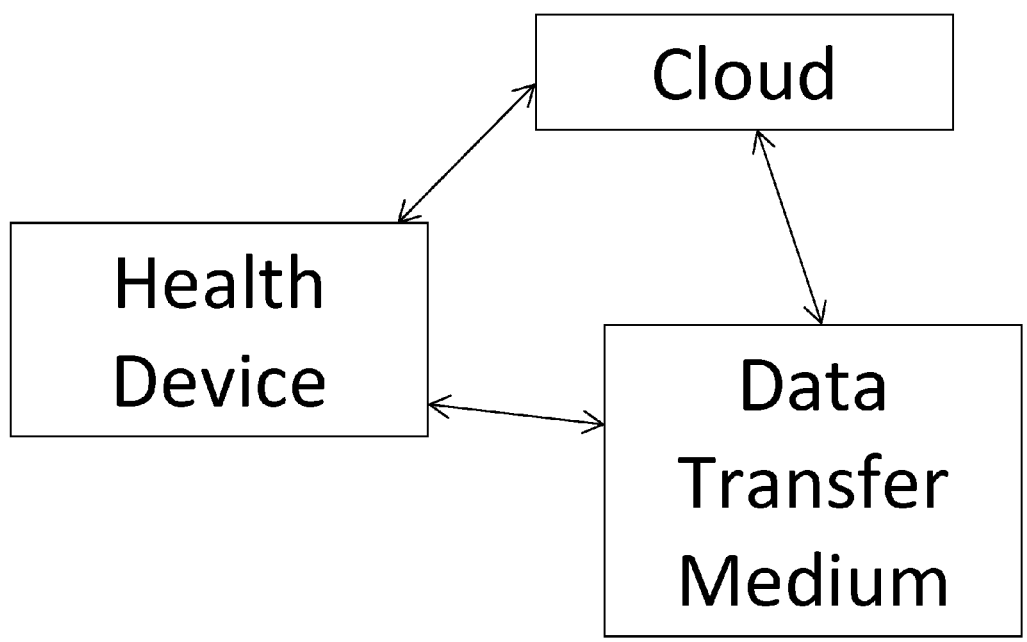
FIG. 1 is a system diagram of a connected health care system, according to multiple embodiments and alternatives.

FIG. 1 shows a connected health care system that allows a user to view and monitor the measured data from a plurality of health devices via a data transfer medium, such as a "smartphone" or computer, and/or a network storage device referred to as the Cloud. Accordingly, the system allows the health devices to transfer data to the data transfer medium and/or the Cloud. Additionally, the data transfer medium may transfer said data to the Cloud for display and manipulation on further data transfer mediums connected to said Cloud. Alternatively, the Cloud may receive said data directly from the health devices and transfer said data to data transfer mediums.

In some embodiments, the data transfer medium comprises a receiver, a transmitter, a data processing unit, and a display. Accordingly, the data processing unit is chosen from the group microprocessor, microcontroller, field programmable gate array (FPGA), digital signal processing unit (DSP), application specific integrated circuit (ASIC), programmable logic, and combinations thereof. The data processing unit comprises a collector, storage medium, and a processor.

Moreover, the storage medium of the data processing unit is comprised of volatile memory and non-volatile memory, wherein volatile memory is used for short-term storage and processing, and non-volatile memory is used for long-term storage. Accordingly, in some embodiments, volatile memory is chosen from the group random-access memory (RAM), dynamic random-access memory (DRAM), double data rate synchronous dynamic random-access memory (DDR SDRAM), static random-access memory (SRAM), thyristor random-access memory (T-RAM), zero-capacitor random-access memory (Z-RAM), and twin transistor random-access memory (TTRAM). Optionally, in some embodiments, non-volatile memory is chosen from the group read-only memory (ROM), programmable read-only memory (PROM), erasable programmable read-only memory (EPROM), electrically erasable programmable read-only memory (EEPROM), flash memory, ferroelectric random-access memory (FeRAM), magnetoresistive random-access memory (MRAM), phase-change memory (PRAM), conductive-bridging random-access memory (CBRAM), silicon-oxide-nitride-oxide-silicon memory (SONOS), resistive random-access memory (RRAM), racetrack memory, nano-random-access memory (NRAM), and Millipede memory.

Additionally, the receiver of the data transfer medium is chosen from the group universal serial bus (USB), serial port, wired Ethernet port, radio frequency, microwave communication, infrared short-range communication, near field communication, and Bluetooth. Often, the receiver of the data transfer medium receives at least one signal from the data transmitter of the connected surface.

Optionally, the data transfer medium is chosen from the group personal computer, tablet computer, mobile phone (i.e. "smartphone"), wearable device (i.e. "smart watch"), television, dedicated system, charging station, network router, and web-enabled server.

Optionally, the transmitter of the data transfer medium is chosen from the group universal serial bus (USB), serial port, wired Ethernet port, radio frequency, microwave communication, infrared short-range communication, near field communication, and Bluetooth.

Additionally, the display of the data transfer medium converts signals into user-readable formats.

In some embodiments, the Cloud is connected to a network, wherein the network is chosen from the group Internet or intranet such that an intranet is a network managed and accessed by an internal organization and is not accessible to the outside world. The network is utilized by the Cloud for receiving and transmitting data. The mode for receiving and transmitting data through the network is chosen from the group universal serial bus (USB), serial port, wired Ethernet port, radio frequency, microwave communication, infrared short-range communication, near field communication, and Bluetooth.

Additionally, the Cloud processes data using at least one microprocessor, at least one microcontroller, or a combination thereof. The storage of data is comprised of volatile memory and non-volatile memory, wherein volatile memory is used for short-term storage and processing, and non-volatile memory is used for long-term storage. Accordingly, volatile memory is chosen from the group random-access memory (RAM), dynamic random-access memory (DRAM), double data rate synchronous dynamic random-access memory (DDR SDRAM), static random-access memory (SRAM), thyristor random-access memory (T-RAM), zero-capacitor random-access memory (Z-RAM), and twin transistor random-access memory (TTRAM). Optionally, non-volatile memory is chosen from the group read-only memory (ROM), programmable read-only memory (PROM), erasable programmable read-only memory (EPROM), electrically erasable programmable read-only memory (EEPROM), flash memory, ferroelectric random-access memory (FeRAM), magnetoresistive random-access memory (MRAM), phase-change memory (PRAM), conductive-bridging random-access memory (CBRAM), silicon-oxide-nitride-oxide-silicon memory (SONOS), resistive random-access memory (RRAM), racetrack memory, nano-random-access memory (NRAM), and Millipede memory.

The Cloud, optionally, is a network server primarily used for storing and processing data. Optionally, the Cloud is comprised of more than one network server such that the network servers operate in conjunction to increase the storing and processing capabilities of the Cloud. Alternatively, the Cloud is provided as a service such that it is physically located at a location separate from the user, and the service provided is the storing and processing of data.

Additionally, the health devices comprise a transceiver that transmits and receives data. The transceiver of the health devices is chosen from the group universal serial bus (USB), serial port, wired Ethernet port, radio frequency, microwave communication, infrared short-range communication, near field communication, and Bluetooth.

Figure 2:
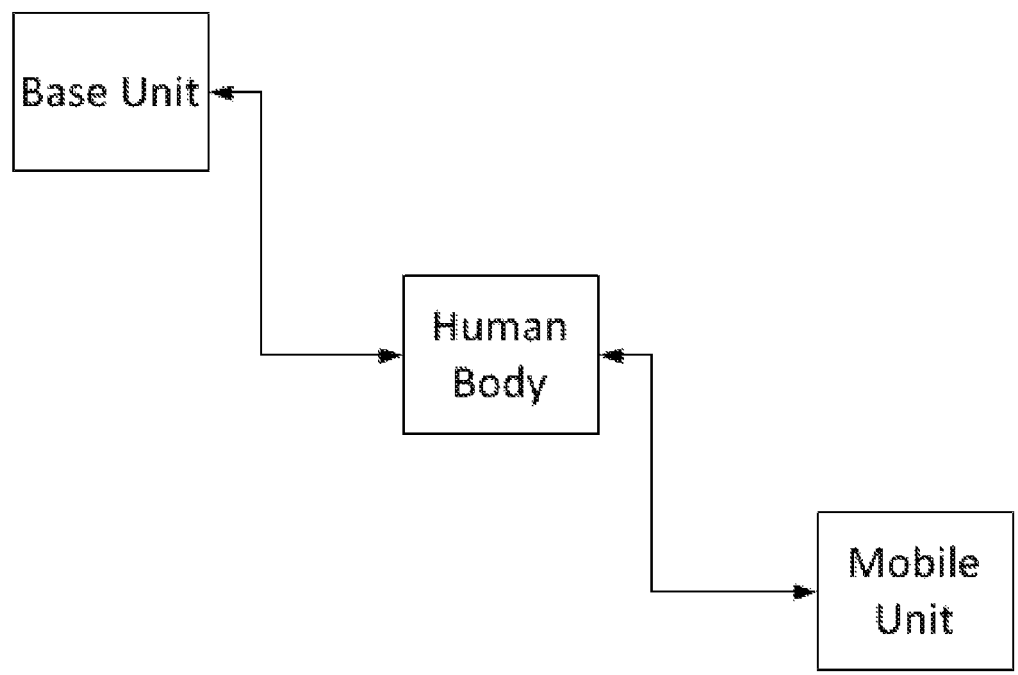
FIG. 2 is a system diagram of a user identification system, according to multiple embodiments and alternatives.

Referring now to FIG. 2, the connected health care system comprises a user identification system, wherein the user identifications system comprises at least one base unit, at least one mobile unit, and the human body. The data processing unit of the base unit operates a capacitive touch sensor that constantly monitors for a touch input. In the instance where the base unit is a connected surface, a touch input is characterized as the user stepping on the connected surface. The data processing unit of the base unit then transmits a signal at a certain frequency to the mobile unit using the human body as a capacitive coupler. The human body's capacitance allows it to transmit signals at different frequencies simultaneously as a capacitive coupler. Additionally, the mobile unit comprises a data processing unit. The mobile unit receives the signal from the base unit indicating the user is in contact with the base unit and transmits a response signal at a different frequency than the signal sent from the base unit. The response signal identifies the mobile unit using a unique identification code, thus identifying the user to the base unit. Since the frequencies of the two signals differ, the signals can be sent simultaneously allowing for simultaneous identification of the user.

Optionally, the mobile unit of the user identification system is a toothbrush comprising a data processing unit such that the toothbrush receives the signal from the base unit through capacitive coupling of the human body. This configuration allows the base unit to identify the user while the user brushes his/her teeth and associate collected data with the identified user. Additionally, the mobile unit of the user identification system is a data transfer medium with a data processing unit. The data transfer medium that is the mobile unit may also be the data transfer medium that is comprised in the connected health system such that it transmits and/or receives data from various devices and acts as the mobile unit of the user identification system. Furthermore, the mobile unit of the user identification system is an attachment to the data transfer medium such that the attachment utilizes the data processing unit of the data transfer medium to communicate with the base unit.

Optionally, the mobile unit is a dedicated system that is used for the sole purpose of identifying the user. Optionally, the mobile unit is an embedded chip in the user's skin such that the user can consistently be identified by the base unit. Optionally, the mobile unit is a tattooed circuit on the user's skin such that the circuit can receive the signal from the base unit and transmit the identification signal.

In some embodiments, the base unit further comprises a speaker that is coupled to the data processing unit of the base unit. Additionally, the data processing unit comprises a voice generator that generates audible speech that is communicated to the user. The voice generator generates speech related to the user's collected data and personal selectable preferences. Optionally, when a user is identified using the user identification system, the voice generator transmits the identified user's related speech through the speaker such that it is audibly transmitted to the user.

Figure 3:
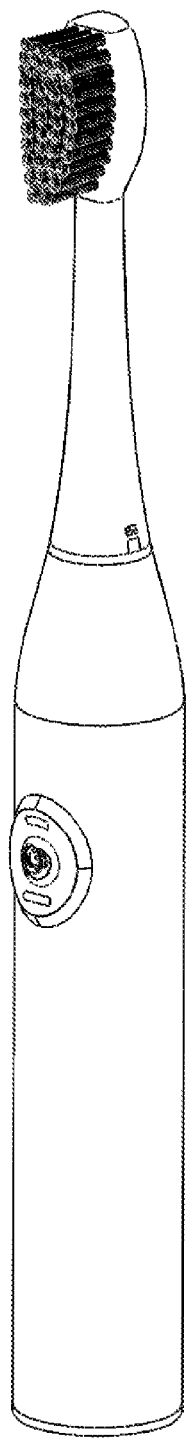
FIG. 3 is a perspective view of a connected toothbrush, according to multiple embodiments and alternatives.

As shown in FIG. 3, the connected health care system comprises at least one toothbrush. A toothbrush is an oral health care implement used for the cleaning of teeth and gingiva, more commonly referred to as gums. The toothbrush is operated in the oral cavity of a human being characterized as the first portion of the alimentary canal that receives food and saliva, and containing a mucous membrane epithelium lining referred to as the oral mucosa. The oral cavity is further characterized as having alveolar arches typically containing teeth, which are either natural, synthetic, or a combination thereof, and used primarily for the preparatory chewing of food for digestion.

A toothbrush comprises a brush head consisting of a plurality of bristles arranged into compact clusters, often referred to as tufts, mounted onto the brush head. Accordingly, the tufts are often mounted in an intentional pattern to facilitate cleaning of teeth and gums. A toothbrush further comprises a handle that extends proximally from the brush head and is used for grasping and movement of the toothbrush. The bristles of the toothbrush are commonly manufactured from either a natural material, synthetic material, or a combination thereof. One example of a natural bristle material is animal hair. An example of a typical synthetic bristle material is Nylon.

In some further embodiments, the toothbrush comprises a flosser. A flosser is an oral health care implement used for the removal of good and dental plaque from teeth, especially between teeth and other places a toothbrush cannot effectively clean. A flosser comprises a flosser head having two parallel protrusions with space between them such that a length of dental floss can be placed between the two protrusions. The dental floss is, most often, held taut by the two protrusions to facilitate proper cleaning. Two common orientations exist for the protrusions in relation to the major axis of a handle including F-shaped wherein the protrusions are generally perpendicular to the major axis of the handle; and the Y-shaped wherein the protrusions are generally parallel to the major axis of the handle.

Inherently, a toothbrush has an associated motion when in use, which is characterized as either manually driven (i.e. manual toothbrush) or electromechanically driven (i.e. powered toothbrush). A manually driven motion is regarded as a motion generated by the user by his/her own power. Conversely, an electromechanically driven motion is characterized as a motion generated by electrical power which is converted to mechanical power used to create the specified electromechanically driven motion. In some embodiments, the electromechanically driven motion is a side-to-side oscillating motion also referred to as vibratory motion. Often, the vibratory motion is generated by an electric motor with an eccentric weight on the drive shaft of the electric motor. In other instances, the vibratory motion is generated by an electrically conductive coil around the outside of a magnetic mass, such that when an alternating current is applied to the coil, the magnetic mass oscillates causing vibration of the toothbrush. In other embodiments, the electromechanically driven motion is a rotation-oscillation motion wherein the head rotates either clockwise or counterclockwise and then rotates in the opposite direction of the first rotation. Additionally, a portion of the brush head may move in a translational motion to provide additional cleaning.

The toothbrush further comprises a data processing unit having at least one collector, a storage medium, and at least one processor, wherein the collector, storage medium, and processor, respectively, collect, store, and process data. Accordingly, the data processing unit is chosen from the group microprocessor, microcontroller, field programmable gate array (FPGA), digital signal processing unit (DSP), application specific integrated circuit (ASIC), programmable logic, and combinations thereof.

Additionally, in some embodiments, the collector of the data processing unit is an electrically conductive wire, wherein the electrically conductive wire receives the electrical output of various sensors.

Moreover, the storage medium of the data processing unit is comprised of volatile memory and non-volatile memory, wherein volatile memory is used for short-term storage and processing, and non-volatile memory is used for long-term storage. Accordingly, volatile memory is chosen from the group random-access memory (RAM), dynamic random-access memory (DRAM), double data rate synchronous dynamic random-access memory (DDR SDRAM), static random-access memory (SRAM), thyristor random-access memory (T-RAM), zero-capacitor random-access memory (Z-RAM), and twin transistor random-access memory (TTRAM). Non-volatile memory is chosen from the group read-only memory (ROM), programmable read-only memory (PROM), erasable programmable read-only memory (EPROM), electrically erasable programmable read-only memory (EEPROM), flash memory, ferroelectric random-access memory (FeRAM), magnetoresistive random-access memory (MRAM), phase-change memory (PRAM), conductive-bridging random-access memory (CBRAM), silicon-oxide-nitride-oxide-silicon memory (SONOS), resistive random-access memory (RRAM), racetrack memory, nano-random-access memory (NRAM), and Millipede memory.

The processor of the data processing unit is chosen from the group microprocessor and micro controller.

Optionally, the toothbrush further comprises at least one transmitter, such that the data can be transmitted to be used by another medium. The data is packaged as at least one signal and transmitted to another medium. The transmitter is chosen form the group universal serial bus (USB), serial port, wired Ethernet port, radio frequency, microwave communication, infrared short-range communication, near field communication, and Bluetooth®.

In some embodiments, the toothbrush further comprises an orientation sensor. Optionally, the orientation sensor is at least one accelerometer, wherein the orientation sensor measures the acceleration of the inertial reference frame relative to itself. The inertial reference frame is defined as the reference frame where an object is in free-fall (i.e. not resisting gravity). Additionally, in some embodiments, the accelerometer is a microelectromechanical system (MEMS) comprised of a cantilever beam with a proof mass where damping results from a residual gas sealed inside the accelerometer. Piezoelectric material is often used to convert the mechanical motion into an electrical signal.

Optionally, the orientation sensor is at least one gyroscope, wherein the orientation sensor measures orientation based on the principle of conservation of angular momentum. Alternatively, the orientation sensor measures orientation based on the physical principle that a vibrating object tends to continue vibrating in the same plane as its support rotates, otherwise known as a vibrating structure gyroscope. In further options, the gyroscope is a microelectromechanical system. Accordingly, the microelectromechanical system that is a vibrating structure gyroscope utilizes a mechanism chosen from the group piezoelectric gyroscope, which uses a piezoelectric material to induce vibration; wine glass resonator, which uses a hemisphere that is driven to resonance; tuning fork gyroscope, which uses two tests masses that are driven to resonance; vibrating wheel gyroscope, which uses a wheel that is driven a fraction of a full turn about its axis; and any combination thereof.

Optionally, the orientation sensor is at least one accelerometer and at least one gyroscope, wherein the accelerometer and the gyroscope operate in conjunction to produce measurement of the full six degrees of freedom. The full six degrees of freedom are characterized as forward/backward, up/down, left/right, pitch, yaw, and roll.

Accordingly, in some embodiments, the data processing unit and the orientation sensor, both of the toothbrush, operate in conjunction to provide means for determining position of the brush head within the oral cavity. The orientation sensor detects the orientation of the toothbrush and transmits a signal to the data processing unit. The collector of the data processing unit receives the signal, and the storage medium stores the signal in the form of data. The processor of the data processing unit operates in conjunction with the storage medium to compare the stored orientation data to previously stored orientation data that correlates to certain positions within the oral cavity. Optionally, the previously stored orientation data that correlates to certain positions within the oral cavity is collected by placing the brush head of the toothbrush at various predetermined positions within the oral cavity, wherein the orientation sensor output is stored at each predetermined position, thus creating correlation data for comparison. Additionally, the toothbrush position data can be correlated to time data provided by RTCC based on motor actuation or capacitive touch sensor data to provide the user with brushing time measurements segmented by different positions within the oral cavity.

In some embodiments, the toothbrush further comprises an oximetry sensor. Optionally, the oximetry sensor is a transmissive pulse oximeter or a reflective pulse oximeter, wherein both types of oximetry sensors detect blood oxygen saturation and/or heart rate.

The transmissive pulse oximeter comprises two distinct sides that are parallel with a space separating the two sides creating a measuring site such that a portion of the human body may be inserted between the two sides. The portion of the human body most often inserted in the measuring site is chosen from the group index finger, middle finger, ring finger, pinky finger, thumb, toe, ear lobe, and nose. Two light-emitting diodes (LED) are at least partially contained on the first parallel side creating an emitter. In some embodiments, the two LEDs produce beams of light at different frequencies, which include the range of about 600-750 nanometers (nm) and the range of about 850-1000 nm such that the frequencies produce red and infrared light, respectively. Additionally, the second parallel side comprises a photo detector positioned to be opposite of the emitter such that the photo detector receives the emitted light that passes through the measuring site. The photo detector determines the amount of red and infrared light received, thus determining the amount of red and infrared light absorbed. Accordingly, the amounts of red and infrared light are transmitted to the data processing unit of the toothbrush.

Optionally, the data processing unit of the toothbrush calculates the ratio of red light to infrared light after the emitted light passes through the measuring site and is received by the photo detector. The calculated ratio is compared to a data bank that relates the calculated ratio to blood oxygen saturation values. The heart rate is further determined by the amount of light absorption of the volume of arterial blood. As the heart pumps blood, the volume of arterial blood increases thus creating a pulsatile change in light absorption. The heart rate is determined by the frequency of pulsatile changes representing heart beats.

Optionally, the reflective pulse oximeter comprises one distinct side, referred to as the contact surface, that comprises both the light emitter and the photo detector such that the emitted light travels into the measuring site and is reflected back to the photo detector. The reflective pulse oximeter allows the user to contact only one surface on the implement. Accordingly, the reflective pulse oximeter may be contacted by the user during the normal operation of the toothbrush.

Accordingly, the reflective pulse oximeter transmits the amounts of red and infrared light received by the photo detector via the transmitter to the data processing unit. Similarly, the ratio of red light to infrared light is calculated and compared to a data bank to correlate the ratio to a blood oxygen saturation value. Additionally, the heart rate of the user is determined in the same manner as described for the transmissive pulse oximeter.

In some embodiments, at least a portion of the oximetry sensor is located on the handle such that the user contacts the oximetry sensor during normal operation of the implement. In some embodiments of the transmissive pulse oximeter, the first and second parallel sides are located on the exterior of the handle such that a user may contact the transmissive pulse oximeter when the toothbrush is fully assembled. In some embodiments, the two parallel sides are parallel to the exterior surface of the handle. Optionally, the two parallel sides are perpendicular to the exterior surface of the handle.

In some embodiments of the reflective pulse oximeter, the contact surface is positioned to be flush with the portions of the handle surrounding the reflective pulse oximeter such that the handle and the reflective pulse oximeter are comprised in a smooth surface. Optionally, the contact surface is positioned to be raised above the portions of the handle surrounding the reflective pulse oximeter such that the reflective pulse oximeter is noticeably distinct from the portions of the handle surrounding it. Optionally still, the contact surface is positioned to be flush with the portions of the handle surrounding the reflective pulse oximeter, and at least a portion of the handle not directly surrounding the reflective pulse oximeter is raised such that the reflective pulse oximeter is located in at least a partial depression indicating where the user shall place his/her thumb for contact with the contact surface.

In some embodiments, the oximetry sensor may be a plurality of transmissive pulse oximeters. In some embodiments, the oximetry sensor may be a plurality of reflective pulse oximeters. Also, in some embodiments, the oximetry sensor may be a combination of at least one transmissive pulse oximeter and at least one reflective pulse oximeter.

In some embodiments, the toothbrush further comprises at least one capacitive sensor. One type of capacitive sensor is a capacitive sensor that works with a frequency change, alternatively referred to as a frequency change capacitive sensor. Optionally, another type of capacitive sensor is a capacitive sensor that works with a capacitive voltage divider, alternatively referred to as a voltage divider capacitive sensor. Both types of capacitive sensors detect the added capacitance of the human body.

The frequency change capacitive sensor comprises a sensor surface, a resistor-capacitor (RC) circuit, and an RC oscillator, wherein the capacitance of the human body introduced by the sensor surface is a parallel capacitance in the RC circuit such that, when the capacitance of the human body is present, the overall capacitance of the RC circuit is altered. The RC oscillator operates at a set frequency controlled by the capacitance of the RC circuit. The sensor surface comes into proximity of the human body, and, consequently, the capacitance of the human body is introduced to the RC circuit by a connection between the sensor surface and the RC circuit such that the capacitance of the human body is a parallel capacitance to the RC circuit. The change in overall capacitance of the RC circuit changes the frequency of the RC oscillator, thus, indicating the human body is in proximity to the sensor surface.

In some embodiments, the frequency of the RC oscillator is compared to a reference value to determine if a change in frequency occurs; therefore, the presence of the human body is detected. Accordingly, three alternatives are presented for performing the comparison between the reference value and the frequency of the RC oscillator. One alternative is to define the reference value as a frequency equivalent to the operating frequency of the RC oscillator when the human body is not in proximity to the sensor surface. In this instance, the reference value and the frequency of the RC oscillator are both input into a frequency comparator, wherein the frequency comparator evaluates if the values are similar; and thus, indicating one way or the other.

Optionally, the second alternative for comparison of the reference value and the frequency of the RC oscillator comprises a frequency-to-voltage converter, a DC voltage reference value, and a comparator, wherein the frequency of the RC oscillator is input to the frequency-to-voltage converter and a voltage corresponding to the frequency is output. The comparator compares the output voltage of the frequency-to-voltage converter to the DC voltage reference value. The DC voltage reference value is equivalent to the output voltage of the frequency-to-voltage converter when the human body is not in proximity to the sensor surface. Accordingly, the comparator outputs a signal consistent with whether the DC voltage reference value is similar to the output of the frequency-to-voltage converter.

Optionally, the third alternative for comparison of the reference value and the frequency of the RC oscillator is to directly measure the frequency of the signal by counting the number of rising or falling edges in a defined time period utilizing a device similar to a microcontroller. In this manner, a baseline operating frequency may be established, and any deviation in frequency beyond a defined threshold will indicate the human body is in proximity to the sensor surface.

The voltage divider capacitive sensor comprises a sensor surface, which provides an analog input; a reference voltage; an analog-to-digital converter (A/DC); and an A/DC capacitor. The A/DC is internally driven to the reference voltage such that the A/DC capacitor is fully charged, and the analog input of the sensor surface is internally grounded such that the sensor surface is fully discharged. Next, the analog input of the sensor surface is internally disconnected from the ground and is internally connected to the A/DC such that the A/DC capacitor will discharge at least a portion of its charge to the sensor surface in order to equal the voltages of the sensor surface and the A/DC capacitor. If the human body is in proximity to the sensor surface, the sensor will appear to have a larger capacitance. Said larger capacitance results in a many time smaller steady-state voltage between the A/DC capacitor and the sensor as compared to the condition when the sensor is in its normal, low capacitance state. The A/DC may measure the analog input and compare it to a threshold to determine if the sensor surface is in proximity to the human body. The voltage provided to the A/DC will decrease in a manner indicative of the human body's proximity to the sensor surface. In some embodiments, the decrease in a manner indicative of the human body's proximity to the sensor surface is significant.

Optionally, the reference voltage, the A/DC, and the A/DC capacitor are comprised in a microcontroller such that circuit comprises a sensor surface with an analog input connected to the microcontroller. The A/DC of the microcontroller converts the voltage provided to the A/DC from an analog signal to a digital signal. The microcontroller determines whether the sensor surface is in proximity to the human body based on the digital signal.

In some embodiments, the sensor surface is a conductive material and covered with an insulator material. Optionally, the insulator material covering the sensor surface is the same material as the outer surfaces of the toothbrush.

An issue resides with the presence of water similarly producing a capacitance that may affect the sensor surface. A desirable advancement of the present invention is to negate the issue of water unwantedly providing a capacitance indicative of the human body's proximity to the sensor surface. Consequently, the negation of water is provided by an effective thickness of insulator material separating the water from the sensor surface. The insulator material allows detection of the sensor surface in proximity to the human body but does not allow detection of the sensor surface in proximity to water.

In some embodiments, the oximetry sensor operates in conjunction with at least one capacitive sensor to improve the quality of oximetry data, namely blood oxygen saturation and heart rate. In an embodiment utilizing a reflective pulse oximeter, a network of capacitive sensors is placed around the outer bounds of the readable area of the oximetry sensor. Most often in the case of a thumb or digit being used for oximetry data, the capacitive sensor detects the presence of said body part as it approaches or passes the threshold of the outer bounds of the readable area. Thus, the capacitive sensor essentially indicates when said body part is no longer in position to obtain an accurate reading of oximetry data. Consequently, the oximetry data can be filtered to determine its accuracy based on the position of the measured body part as it coincides with the capacitive data at any given time. Alternatively, the capacitive data can be used to determine the measured body part is present on the oximetry sensor in a measurable capacity, and the capacitive data can control the activity of the oximetry sensor, such as the "on" and "off" states. Thus, the oximetry sensor shall be "on" when the body part is positioned for measurement and "off" when it is not.

In some embodiments, the toothbrush further comprises at least one pressure sensor to determine if the pressure exerted on the implement is excessive in relation to its intended use. Optionally, the pressure sensor may be constructed from two parallel conductive plates separated by an insulator such that, in the active portion of the sensor, the insulator allows for an air gap between the parallel plates, referred to as a parallel plate capacitive sensor. For example, the insulator comprises a hole that allows for an air gap between the parallel plates. Forces acting perpendicular to the plane of the parallel plates in the active region deform one conductor or both conductors. Accordingly, the parallel plates move closer together due to deformation, thus, increasing the capacitance of the sensor. Additionally, the bristles comprised in the brush head are operatively attached to at least one of the parallel plates, wherein applied pressure may be detected by the force exerted by the bristles on the brush head.

Optionally, the pressure sensor may be at least one strain gage mounted on a section of the load bearing portion of the toothbrush, such as the neck of the toothbrush. Excessive pressure exerted by brushing the user's teeth causes deflection in the neck of the toothbrush, which creates a strain. Consequently, the deflection in the neck of the toothbrush causes a strain in the strain gage, which results in a measurable variation of a certain electrical property in the strain gage, such as electrical impedance. Further still, additional strain gages may be used to determine the force exerted by brushing in more than one direction providing the user with a more enhanced overview the source of excess pressure while brushing.

Alternatively, in cases where the toothbrush exhibits an electromechanically driven motion, the pressure sensor may be based on variations in electrical properties of the electric motor, especially in instances when the shaft of said motor is coupled in some way to the brush head of the toothbrush. The threshold for excessive pressure while brushing has an associated current draw exhibited by the electric motor, such that added force on the shaft of the motor requires more current draw to maintain the motors capacity. Consequently, the current draw of the electric motor may be monitored to determine when excessive pressure is applied to the brush head during brushing. Further, when the threshold for excessive pressure is reached, the motor can respond in a fashion as to alert the user that excessive pressure is being used while brushing.

Optionally, in cases where the toothbrush exhibits an electromechanically driven motion, the pressure sensor may be based on variations in magnetic properties of the electric motor. The magnetism of the electric motor varies as the current draw fluctuates due to loading on the electric motor. Consequently, the variations in magnetism are monitored to determine when magnetic properties indicative of excessive pressure are present. The variations in magnetism are monitored with the use of at least one Hall effect sensor or the like. Alternatively, at least one magnet is placed in the neck of the brush such that when mechanical displacement of the magnet occurs the magnetism measured by at least one Hall effect sensor varies. Therefore, the Hall effect sensor can determine when the magnetic properties of the mechanically displaced magnet are indicative of excessive pressure applied to brush head during brushing. Further, when the magnetic properties are indicative of excessive pressure, the motor can respond in a fashion as to alert the user that excessive pressure is being used while brushing.

In some embodiments, the toothbrush further comprises at least one temperature sensor. The temperature sensor is chosen from the group thermocouple, thermistor, resistance temperature detector (RTD), infrared temperature sensor, thermopile, thermostat, and silicon bandgap temperature sensor.

In some embodiments, the temperature sensor is at least one thermocouple, wherein the thermocouple comprises two different conductors, typically metal alloys, that produce a voltage proportional to a temperature difference between either end of the pair of conductors. Optionally, the temperature sensor is at least one thermistor, wherein the thermistor is a resistor that has a certain resistance, which varies significantly with temperature. Thermistors are generally comprised of a ceramic or polymer material.

Optionally, the temperature sensor is at least one resistance temperature detector (RTD), wherein the RTD exploits a predictable change in electrical resistance that is dependent upon a change in temperature. Often, the material of the RTD is platinum. Alternatively, the temperature sensor is at least one infrared temperature sensor, wherein the temperature of an object is determined by a portion of thermal radiation referred to as blackbody radiation emitted by the object, such that knowing the infrared energy emitted and the object's emissivity allows for the determination of the object's temperature.

Optionally, the temperature sensor is at least one thermopile, wherein the thermopile converts thermal energy into electrical energy and is comprised of one or more thermocouples connected in series or parallel. Optionally, the temperature sensor is at least one thermostat, wherein the thermostat comprises two different metals that are bonded together to form a bi-metallic strip, such that the difference in linear expansion rates causes a mechanical bending movement when heat is applied. In some embodiments, the temperature sensor is at least one silicon bandgap temperature sensor, wherein the forward voltage of a silicon diode is dependent on temperature, and the temperature is determined by comparing bandgap voltages at two different currents.

Consequently, the temperature sensor and the data processing unit, both of the toothbrush, operate in conjunction to provide data indicative of user core body temperature, wherein the user core body temperature is a user's operating temperature, which can be indicative of problems experienced by the user.

In some embodiments, the toothbrush further comprises a wireless charging system including a charging base. The charging base comprises an inductive coil that receives current and transmits waves at a certain oscillating frequency. The inductive coil of the charging base is referred to as the transmitting coil. In this instance, the toothbrush comprises a second inductive coil within the body of the toothbrush, referred to as the receiving coil. The receiving coil receives the transmitted waves from the transmitting coil and uses the transmitted to charge at least one storage cell via a charging chip.

Figure 4:
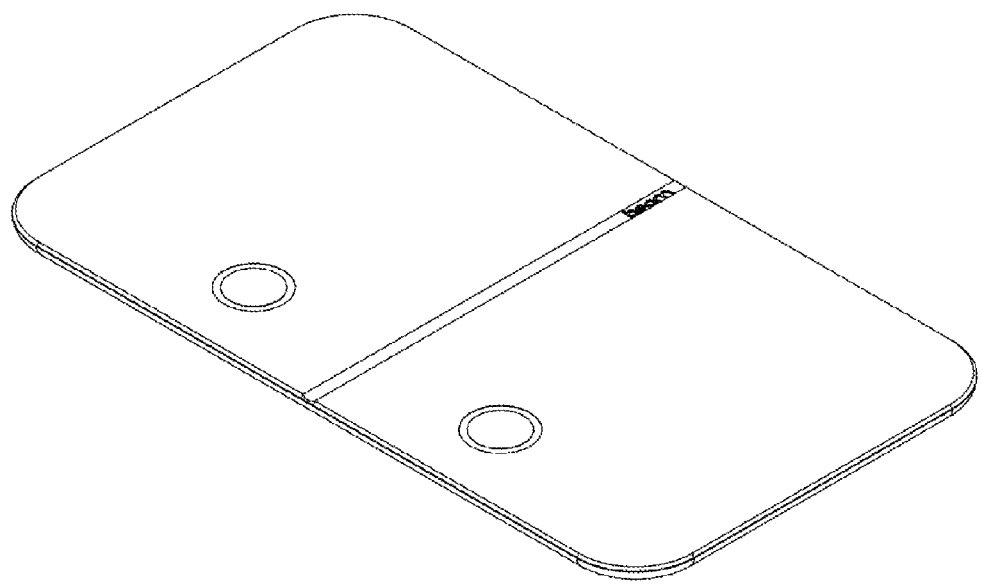
FIG. 4 is a perspective view of a connected surface with sensors, according to multiple embodiments and alternatives.

Referring now to FIG. 4, the connected health care system further comprises at least one connected surface with sensors. A surface allows a user to stand on said surface during normal daily activities, such as tooth brushing, drying after bathing, etc. Said surface may be chosen from the group flooring, bath mat, weight scale, rug, dedicated system, and any combination thereof. Flooring is the walking surface of a room and may consist of various materials including wood, carpet, etc. A bath mat is a mat used on the floor of a bathroom that provides a warm, non-slip surface and may absorb certain amounts of water. A weight scale is a measuring device for determining the weight or mass of a person. A rug is a textile floor covering consisting of an upper layer attached to a backing. A dedicated system is a dedicated surface designed for the specific purpose of collecting data through various sensors and transmitting said data.

Additionally, the connected surface of the present invention comprises a data processing unit having at least one collector, a storage medium, and at least one processor, wherein the collector, storage medium, and processor, respectively, collect, store, and process data. Accordingly, the data processing unit is chosen from the group microprocessor, microcontroller, field programmable gate array (FPGA), digital signal processing unit (DSP), application specific integrated circuit (ASIC), programmable logic, and combinations thereof.

Additionally, in some embodiments, the collector of the data processing unit is an electrically conductive wire, wherein the electrically conductive wire receives the electrical output of various sensors.

Moreover, the storage medium of the data processing unit is comprised of volatile memory and non-volatile memory, wherein volatile memory is used for short-term storage and processing, and non-volatile memory is used for long-term storage. Accordingly, volatile memory is chosen from the group random-access memory (RAM), dynamic random-access memory (DRAM), double data rate synchronous dynamic random-access memory (DDR SDRAM), static random-access memory (SRAM), thyristor random-access memory (T-RAM), zero-capacitor random-access memory (Z-RAM), and twin transistor random-access memory (TTRAM). Non-volatile memory is chosen from the group read-only memory (ROM), programmable read-only memory (PROM), erasable programmable read-only memory (EPROM), electrically erasable programmable read-only memory (EEPROM), flash memory, ferroelectric random-access memory (FeRAM), magnetoresistive random-access memory (MRAM), phase-change memory (PRAM), conductive-bridging random-access memory (CBRAM), silicon-oxide-nitride-oxide-silicon memory (SONOS), resistive random-access memory (RRAM), racetrack memory, nano-random-access memory (NRAM), and Millipede memory.

The processor of the data processing unit is chosen from the group microprocessor and micro controller.

Furthermore, the connected surface comprises at least one data transmitter, such that the data can be transmitted to be used by another medium and data can be received from another medium. The data is packaged as at least one signal and transmitted to another medium. The data transmitter is chosen form the group universal serial bus (USB), serial port, wired Ethernet port, radio frequency, microwave communication, infrared short-range communication, near field communication, and Bluetooth®.

In some embodiments, the connected surface further comprises an oximetry sensor. Optionally, the oximetry sensor is a reflective pulse oximeter or a transmissive pulse oximeter, wherein both types of oximetry sensors detect health statistics chosen from the group blood oxygen saturation, heart rate, respiration rate, blood pressure, blood flow, and any combination thereof.

The transmissive pulse oximeter comprises two distinct sides that are parallel with a space separating the two sides creating a measuring site such that a portion of the human body may be inserted between the two sides. The portion of the human body most often inserted in the measuring site is chosen from the group index finger, middle finger, ring finger, pinky finger, thumb, toe, ear lobe, and nose. Two light-emitting diodes (LED) are at least partially contained on the first parallel side creating an emitter. In some embodiments, the two LEDs produce beams of light at different frequencies, which include the range of about 600-750 nanometers (nm) and the range of about 850-1000 nm such that the frequencies produce red and infrared light, respectively. Additionally, the second parallel side comprises a photo detector positioned to be opposite of the emitter such that the photo detector receives the emitted light that passes through the measuring site. The photo detector determines the amount of red and infrared light received, thus determining the amount of red and infrared light absorbed. Accordingly, the amounts of red and infrared light are transmitted to the data processing unit of the connected surface.

Optionally, the data processing unit of the connected surface calculates the ratio of red light to infrared light after the emitted light passes through the measuring site and is received by the photo detector. The calculated ratio is compared to a data bank that relates the calculated ratio to blood oxygen saturation values. The heart rate is further determined by the amount of light absorption of the volume of arterial blood. As the heart pumps blood, the volume of arterial blood increases thus creating a pulsatile change in light absorption. The heart rate is determined by the frequency of pulsatile changes representing heart beats.

Optionally, the reflective pulse oximeter comprises one distinct side, referred to as the contact surface that comprises both the light emitter and the photo detector such that the emitted light travels into the measuring site and is reflected back to the photo detector. The reflective pulse oximeter allows the user to contact only one surface on the connected surface. Accordingly, the reflective pulse oximeter may be contacted by the user during the normal use of the connected surface.

Accordingly, the reflective pulse oximeter transmits the amounts of red and infrared light received by the photo detector via the transmitter to the data processing unit. Similarly, the ratio of red light to infrared light is calculated and compared to a data bank to correlate the ratio to a blood oxygen saturation value. Additionally, the heart rate of the user is determined in the same manner as described for the transmissive pulse oximeter.

In some embodiments of the reflective pulse oximeter, the contact surface is positioned to be flush with the portions of the connected surface surrounding the reflective pulse oximeter such that the handle and the reflective pulse oximeter are comprised in a smooth surface. Optionally, the contact surface is positioned to be raised above the portions of the connected surface surrounding the reflective pulse oximeter such that the reflective pulse oximeter is noticeably distinct from the portions of the connected surface surrounding it. Optionally still, the contact surface is positioned to be flush with the portions of the connected surface surrounding the reflective pulse oximeter, and at least a portion of the connected surface not directly surrounding the reflective pulse oximeter is raised such that the reflective pulse oximeter is located in at least a partial depression indicating where the user shall place his/her body part for contact with the contact surface.

In some embodiments, the oximetry sensor may be a plurality of transmissive pulse oximeters. In some embodiments, the oximetry sensor may be a plurality of reflective pulse oximeters. Also, in some embodiments, the oximetry sensor may be a combination of at least one transmissive pulse oximeter and at least one reflective pulse oximeter.

Furthermore, the connected surface comprises an ultrasonic sensor that measures the bone density of the user from the heel of the foot. The ultrasonic sensor includes at least one ultrasonic transducer and at least one ultrasonic detector. The ultrasonic transducer converts energy into ultrasound and emits said ultrasound, which is sound waves above the normal audible range of human hearing, typically with a frequency of 20 MHz or greater. Optionally, the ultrasonic transducer is a piezoelectric transducer that converts electrical energy into ultrasound by applying an alternating current (AC) across piezoelectric material, which holds the property of changing size when a voltage is applied to it. The application of alternating current to piezoelectric material provides a high frequency oscillation of the piezoelectric material. Consequently, very high frequency sound waves are produced by the high frequency oscillation of the piezoelectric material.

Additionally, the ultrasonic detector is a piezoelectric detector that receives ultrasound causing the piezoelectric material to oscillate at a high frequency, thus producing an electrical voltage indicative of the frequency of the ultrasound. Optionally, the piezoelectric transducer and the piezoelectric detector utilize the same body of piezoelectric material. Accordingly, the combined embodiment of the piezoelectric transducer and the piezoelectric detector is a piezoelectric transceiver, which performs the functions of both the piezoelectric transducer and the piezoelectric detector comprised in one singular body of piezoelectric material. Conversely, the piezoelectric transducer and the piezoelectric detector utilize separate bodies of piezoelectric material.

The piezoelectric material is chosen from the group Quartz, Berlinite (AlPO$_4$), Potassium sodium tartrate, Topaz (Al$_2$SiO$_4$(F, OH)$_2$), Gallium orthophosphate (GaPO$_4$), Langasite (La$_3$Ga$_5$SiO$_{14}$), Barium titanate (BaTiO$_3$), Lead titanate (PbTiO$_3$), Lead zirconate titanate (Pb[Zr$_x$Ti$_{1-x}$]O$_3$, $0 \leq x \leq 1$), Potassium niobate (KNbO$_3$), Lithium niobate (LiNbO$_3$), Lithium tantalite (LiTaO$_3$), Sodium tungstate (Na$_2$WO$_3$), Sodium potassium niobate (NaKNb), Bismuth ferrite (BiFeO$_3$), Sodium niobate (NaNbO$_3$), and Polyvinylidene fluoride (PVDF).

Optionally, the ultrasonic transducer is a magnetostrictive transducer comprising a magnetostrictive material, magnetizing coil, and magnetic enclosure, wherein the combination of the three elements completes a magnetic circuit. Magnetostrictive transducers utilize the magnetostrictive property of the magnetostrictive material to convert the magnetic energy of a magnetic field to ultrasound, which is sound waves above the normal audible range of human hearing, typically with a frequency of 20 MHz or greater. The magnetostrictive property is a material property, common to ferromagnetic materials, where the material is divided into uniform magnetic polarization domains, such that when a magnetic field is applied said domains shift and rotate causing the magnetostrictive material to change size at a high frequency, thus generating high frequency sound waves or ultrasound. In a magnetostrictive transducer, the magnetic field is provided by the magnetizing coil wrapped around the magnetostrictive material. The magnetic field of the magnetizing coil is produced by the input of electrical energy into the coil.

In some embodiments, the ultrasonic detector is a magnetostrictive detector comprising a magnetostrictive material, magnetizing coil, and magnetic enclosure, wherein the combination of the three elements completes a magnetic circuit. In the same manner as the magnetostrictive transducer, the magnetostrictive detector utilizes the magnetostrictive property of the magnetostrictive material to convert ultrasound to magnetic energy, which alters the magnetic field of the magnetizing coil, thus altering the electrical energy output of the magnetostrictive detector.

The magnetostrictive material is chosen from the group Cobalt, Terfenol-D, and Metglas 2605SC. In some embodiments, the magnetizing coil is manufactured from an electrically conductive material. Additionally, in some embodiments, the magnetostrictive transducer and the magnetostrictive detector utilize the same magnetostrictive material, magnetizing coil, and magnetic enclosure, consequently embodied as a magnetostrictive transceiver. Optionally, the magnetostrictive transducer and the magnetostrictive detector have separate magnetostrictive materials, magnetizing coils, and magnetic enclosures.

Optionally, the ultrasonic transducer is a capacitive actuator comprising two conductive plates on either side of a dielectric material, wherein electrical energy is passed from one conductive plate through the dielectric material to the second conductive plate. The passing of electrical energy across the conductive plates causes the conductive plates to acquire opposite charges, which further causes an attractive force to exist between the conductive plates. Electrical energy in the form of alternating current provides high frequency oscillation of the capacitive actuator, thus converting electrical energy into ultrasound.

In some embodiments, the ultrasonic detector is a capacitive actuator having the same properties as stated above. The process is reversed in the instance of the ultrasonic detector, such that ultrasound is received that affects the oscillation of the capacitive actuator, and the electrical energy passed between the two conductive plates through the dielectric material is altered as a result.

In some embodiments, the ultrasonic sensor is a microelectromechanical system (MEMS). A microelectromechanical system is characterized as a system comprising miniaturized mechanical and electro-mechanical elements that are fabricated using the techniques of microfabrication. A microelectromechanical system is further characterized as comprising miniaturized structures, referred to as microstructures; miniaturized sensors, referred to as microsensors; miniaturized actuators, referred to as micro actuators; and microelectronics. Microsensors and microactuators are commonly referred to as microtransducers, which are miniaturized devices that convert energy from one medium to another, such as mechanical to electrical.

Accordingly, the ultrasonic transducer transmits ultrasound through the heel of the user into the user's bones and the ultrasound is reflected. The reflected ultrasound is received by the ultrasonic detector. The time between transmission and detection of ultrasound, essentially the speed of sound, is correlated to reference bone density data stored by the data processing unit.

In some embodiments, the connected surface comprises a weight sensor to collect weight and balance measurements of the user. The weight sensor is chosen from the group at least one strain gage, electronic analytical scale, capacitive scale, and any combination thereof. Accordingly, the weight sensor distributed across the connected surface such that weight measurements are made when the user is standing on the connected surface at any orientation. Further, the distributed weight sensor provides for balance measurement based on the differing pressure applied by the user's individual feet such that more pressure from one foot may indicate poor balance.

A strain gage is comprised of an insulating flexible backing with a metallic foil pattern affixed and is attached to the connected surface in a proper place with an adhesive, such as cyanoacrylate. As a load is applied to the connected surface, the connected surface deforms causing the foil of the strain gage to deform that results in an electrical resistance change, which is typically measured using a Wheatstone bridge. The resistance change is converted into a strain value using a gage factor and the strain value is used to calculate the load on the connected surface, which provides the weight of the user providing the load.

An electronic analytical scale measures the load on the connected surface by countering the load applied using an electromagnet to generate a force. The measurement of the counter force applied by the electromagnet and the electromagnet itself are often comprised in an electromagnetic force restoration sensor.

A capacitive scale comprises a capacitive sensor that is constructed from two parallel conductive plates separated by an insulator such that, in the active portion of the sensor, the insulator allows for an air gap between the parallel plates. Forces acting perpendicular to the plane of the parallel plates in the active region deform one or both conductors. Accordingly, the parallel plates move closer together or farther apart due to deformation, thus, changing the capacitance of the sensor. The change in capacitance is scaled by a reference factor that provides the weight of the item causing the capacitance change.

Optionally, the connected surface further comprises at least one thermal imaging sensor, wherein the thermal imaging sensor is located on the underside of the connected surface such that its field of view comprises the user standing on the connected surface. The thermal imaging sensor detects radiation in the infrared of the electromagnetic spectrum, which is roughly 9,000-14,000 nanometers. The amount of radiation emitted increases with temperature, thus providing a differentiation between hot and cold areas. Accordingly, the thermal imaging sensor allows the data processing unit to identify hot spots on the user's body that correlate to potential ulcers. Often, foot ulcers are a symptom of diabetes and indicate the onset of more serious medical ailments.

In some embodiments, the connected surface further comprises a galvanic skin response sensor that measures the moisture level of the user's skin via the electrical conductance of the skin. The galvanic skin response sensor measures the electrical conductance between two points by transmitting a small amount of current through the body that follows two paths, which are the surface of the skin and through the body. The conductance varies based on the response of the skin and muscle tissue to the stimuli. The conductance resulting from the test is correlated to reference values that can be personalized to individual users. The correlation to reference values provides indicators of stress and anxiety levels the user is experiencing.

In some embodiments, the connected surface further comprises a body fat sensor that measures percent body fat of the user as the user stands on the connected surface. The body fat sensor is integrated into the connect surface such that use of the body fat sensor does not require the user to perform extra steps beyond standing on the connected surface. Percent body fat is an effective statistic in contributing to an overall understanding of overall health, especially when paired with weight and balance measurements.

Optionally, the body fat sensor utilizes the method of near-infrared interactance comprising at least one infrared emitter and at least one photo detector. A beam of infrared light is transmitted into the user's body, often through the foot. The infrared light is reflected by non-fatty tissue and absorbed by fat tissue. The photo detector captures the reflected infrared light. The ratio of the infrared light returned to the photo detector to the infrared light emitted by the infrared emitter is correlated to the percentage body fat of the user using reference values stored by the data processing unit.

Further variations of the body fat sensor include electrical impedance analysis comprising at least two conductors. A small electric current is sent through the user's body and the impedance between the conductors is measured. The impedance is correlated to body fat percentage of the user based on the user's gender, age, weight, and reference values. In general, fat is anhydrous and a poor conductor of electric current. Conversely, non-fatty tissue, water, and electrolytes are good conductors of electric current. Consequently, the percent body fat increases with increased impedance, thus providing a method of measuring percent body fat.

In some embodiments, the connected surface further comprises an electrocardiogram sensor that measures the rate and regularity of heartbeats by interpreting the electrical activity of the heart over a period of time. Accordingly, electrodes contact the skin and the electrical activity of the heart is recorded across the thorax of the user. In some cases of the connected surface, electrodes contact the skin at the user's feet and the measurement is taken using two electrodes.

Additionally, the electrical activity data measured by the electrocardiogram is transmitted to the data processing unit of the connected surface. Optionally, the electrical activity data is transmitted by the data transmitter of the connected surface to the data transfer medium and/or the Cloud. Alternatively, the electrical activity data is processed by the data processing unit of the connected surface and then transmitted to the data transfer medium and/or the Cloud. The processed electrical activity data shall present health statistics including heart rate, heart electrical activity, blood pressure variation, and other associated health statistics.

Consequently, electrical activity data of the electrocardiogram and oximetry data of the oximetry sensor are correlated to provide a measurement of systolic blood pressure using Pulse Arrival Time. The Pulse Arrival Time is derived by correlating certain features of the electrical activity data and certain features of the oximetry data with respect to time.

Optionally, the connected surface acts as the base unit in the user identification system. The electrodes of the electrocardiogram and the data processing unit work with capacitive coupling of the human body to transmit and receive signals from the mobile unit.

Figure 5:
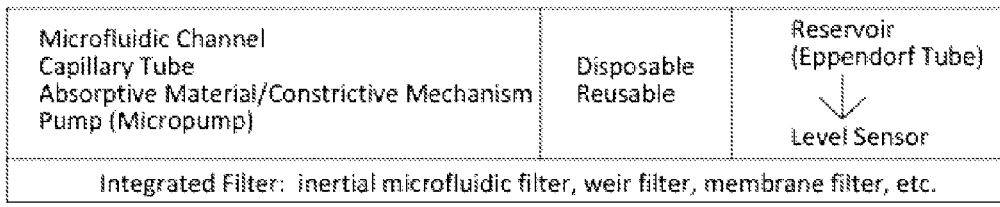
FIG. 5 is a flow chart of a salivary diagnostic system, according to multiple embodiments and alternatives.
Figure 5:
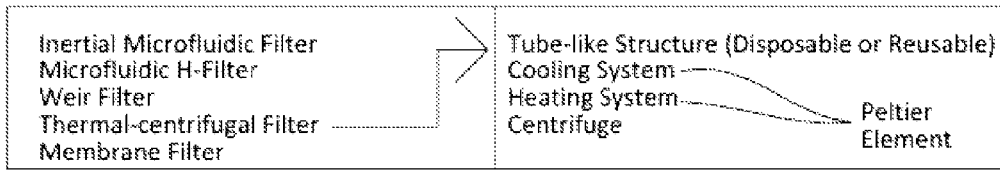
Figure 5:
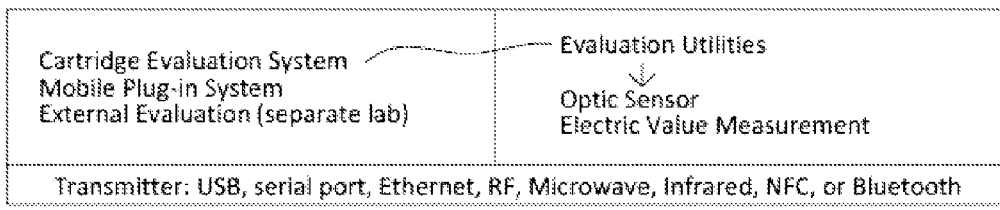
Figure 5:
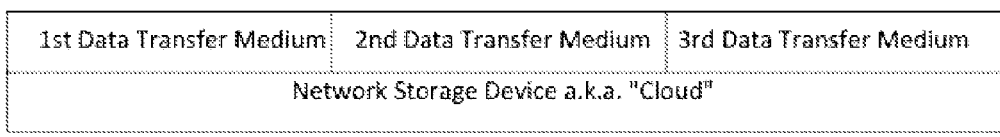

As shown in FIG. 5, the connected health care system further comprises salivary diagnostic systems including a collection system, a filter system, an evaluation system, and a reporting system. The salivary diagnostic systems are interchangeably configured to be coupled by various methods and steps.

In some embodiments, a collection system is configured to collect at least one saliva sample from the oral cavity of a user for the detection and diagnosis of disease. Generally, the collection system collects a specified amount of saliva from a user comprising a saliva sample that is then used by various other salivary diagnostic systems. The specified amount of saliva is standardized in some instances, and varied in accordance with a specific test in other instances. The saliva sample obtained by the collection system is transferred to a filter system, an evaluation system, or both a filter system and an evaluation system, consecutively. Accordingly, a collection system comprises multiple embodiments of collection methods and associated structures.

In some embodiments, the collection system is at least one microfluidic channel and a reservoir, wherein at least one microfluidic channel is fluidly coupled to the reservoir. A microfluidic channel is characterized as having at least one solid side configured to create a depression in a solid surface such that the microfluidic channel can retain collected fluid; the fluid is, often, oral fluid. A microfluidic channel is further characterized as handling small fluid volumes, including volumes less than Pico liters, and providing an interface that exhibits the microscale behavior of fluids. Several methods of collecting fluid via a microfluidic channel exist including both passive and active fluid control techniques. One passive fluid control technique utilized for the collection of fluid via the microfluidic channel is capillary action. Several active fluid control techniques utilized for the collection of fluid via the microfluidic channel are rotary drives, micro pumps, and micro valves.

In some embodiments, the collection system is a capillary tube and a reservoir, wherein a capillary tube is fluidly coupled to a reservoir. A capillary tube uses capillary action to draw a fluid from a surface into the tube to be transported. Capillary action forces the fluid into the tube due to the combination of surface tension and adhesive forces between the fluid and the tube.

In some embodiments, the collection system is an absorptive material, a constriction mechanism, and a reservoir. An absorptive material is fluidly coupled to the oral fluid contained in or expelled from the oral cavity of a user. The fluid coupling allows for the process of absorption to move the oral fluid into the interstitial space of the absorptive material up to the point of saturation. Prior to or at the point of saturation, the constrictive mechanism applies force to the absorptive material, thus constricting the absorptive material. As the absorptive material is constricted, the oral fluid is expelled from the absorptive material into the fluidly coupled reservoir for storage.

In some embodiments, the collection system is a pump fluidly coupled to a reservoir, wherein the pump transfers fluid to the reservoir. Various embodiments of pumps exist in the present invention. A pump of the collection system is chosen from the group gear pump, screw pump, rotary vane pump, plunger pump, diaphragm pump, piston displacement pump, radial piston pump, rotary lobe pump, progressive cavity pump, regenerative pump, peristaltic pump, pulser pump, centrifugal pump, radial-flow pump, axial-flow pump, mixed-flow pump, and valveless pump.

In some embodiments, the collection system is disposable, wherein the collection system is disposed of following its use. Accordingly, a new collection system is used every time a saliva sample is collected. Alternatively, the collection system is reusable, wherein the collection system is sufficiently cleaned following its use. Accordingly, the same collection system is used to collect multiple saliva samples over a period of time.

In some embodiments, the reservoir of the collection system comprises a fluid level sensor that detects the level of the oral fluid transferred to the reservoir. The fluid level sensor further detects when the oral fluid level is at a specified level. Optionally, the specified level corresponds to a level sufficient for use with the salivary diagnostic system. Additionally, the fluid level sensor sends a signal indicating the specified level has been attained. Accordingly, this signal leads to cessation of oral fluid collection by physically stopping collection or signaling to a user to stop collection.

The fluid level sensor is chosen from the group displacement level gauge, load cell, magnetic level gauge, capacitance transmitter, magnetostrictive level transmitter, ultrasonic level transmitter, radar level transmitter, and any combination thereof.

In some embodiments, the collection system does not comprise a reservoir and is instead fluidly coupled to a filter system. Accordingly, the oral fluid collected by the collection system is not stored in a reservoir but transferred directly to a fluidly coupled filter system.

In some embodiments, a filter system is configured to filter at least one saliva sample transferred from the collection system of the salivary diagnostic system for the detection and diagnosis of disease. Generally, the filter system filters the saliva sample such that the saliva sample exits the filter system in an optimum condition for evaluation. Optionally, the optimum condition for the saliva sample varies in accordance with the desired evaluation. However, in some embodiments, the optimum condition for the saliva sample is standardized such that desired evaluations are configured to use a standardized saliva sample provided by the filter system. Further still, in some embodiments, the optimum condition for the saliva sample provided by the filter system is, consequently, the optimum condition for a wide array of desired evaluations.

In some embodiments, the filter system is at least one inertial microfluidic filter. An inertial microfluidic filter comprises a rectangular channel cross-section optimized in size to filter specific sizes of particles, wherein variation of the size of the rectangular channel results in variation in the particle size filtered. The inlet of the rectangular channel provides a singular path for flow of the fluid and the particles to be filtered. Accordingly, the outlet of the rectangular channel comprises a four way junction, wherein the fluid and particles to be filtered enter the junction through a singular path consistent with the inlet. The remaining three flow paths of the four way junction radiate from the junction entrance at certain angular positions in relation to the junction entrance. In some embodiments, the remaining three flow paths radiate at 90° from the junction entrance, such that the remaining three flow paths are positioned at 90°, 180°, and 270° from the direction of flow of the junction entrance. In the present invention, the desired filtered fluid flows to the 180° channel such that the desired filtered fluid flows along a 180° or linear path through the four way junction. The filtered fluid then flows through additional filters within the filter system or is readied for the evaluation system. Additionally, the particles to be filtered flow to the 90° and 270° channels, which are perpendicular to the junction entrance. The particles are discarded after filtration.

In some embodiments, the filter system is at least one microfluidic H-filter. A microfluidic H-filter comprises two inlet channels and an expanding outlet channel, often in the shape of a "V." Further, a microfluidic H-filter comprises a mixing channel between the two inlet channels and the outlet channel, such that the combination of all the channels resembles the letter "H." One inlet channel transports the fluid to be filtered; oral fluid in the present invention. The second inlet channel transports a collection buffer to be mixed with the fluid to be filtered. The mixing channel is optimized with respect to the diffusion coefficient of the fluid, the necessary contact time between the fluid and the buffer, and the geometry and dimensions of the mixing channel. The mixing of the buffer with fluid and the diffusion properties of both result in a purified sample of the desired fluid exhibited on one side of the outlet channel, such that the purified sample is extracted from the outlet channel on the corresponding side with the purified sample. If the Reynolds number is low, then an intervening membrane is not required. In some embodiments, a microfluidic H-filter is pump-driven such that a micro-pump facilitates the flow of fluids in the H-filter. Optionally, a microfluidic H-filter is made from paper and known has a paper H-filter, which does not require the use of a micro-pump to operate efficiently.

In some embodiments, the filter system is at least one weir, collectively a weir filter. In general, a weir filter comprises a channel for fluid flow and a flow barrier that allows a certain amount of fluid to pass over it. In some embodiments, the channel is comprised of at least two different levels, wherein the levels are separated by the flow barrier and the level after the flow barrier is lower than the level before the flow barrier. Accordingly, the fluid flows through the upper level of the channel into the flow barrier, wherein a portion of the fluid flows over the flow barrier and falls to the lower level of the channel. Additionally, the fluid flow that encounters the flow barrier, the fluid that does not flow over the flow barrier, is stopped and held by the flow barrier, often in a pool.

In some embodiments, the fluid flow that encounters the flow barrier is comprised of larger particulates, such the larger particulates travel to the bottom of the flow. Additionally, the larger particulates are not desirable for saliva diagnostic evaluation. Therefore, the collection of larger particulates by the flow barrier creates an oral fluid filter that allows only small particulate saliva to travel to the lower level of the channel. Optionally, in some embodiments, the flow barrier comprises a membrane that allows small particulates and the fluid to pass through, which allows for fluid to ultimately pass through to the lower level of the channel. In some embodiments, multiple levels are incorporated into the channel along with multiple flow barriers, wherein each level and flow barrier is optimized to filter certain size particulates from the fluid.

In some embodiments, the filter system is a thermal-centrifugal filter, wherein the saliva sample is frozen after being transferred from the collection system. After a specified period of time, the saliva sample is thawed with or without the aid of a heating system. Accordingly, the freezing and thawing process of filtering the saliva facilitates the separation of mucus, cellular debris, and food particles from the desired portion of the saliva sample. The thawed saliva sample is then centrifuged for a specified amount of time at a specific angular velocity. After being centrifuged, the saliva sample is adequately separated, wherein the desired saliva is on the top of the sample and the undesired substances at the bottom of the sample. Accordingly, the desired saliva is removed from the sample and is ready for evaluation by the evaluation system.

In some embodiments, a thermal-centrifugal filter comprises at least one cooling system, at least one heating system, and at least one centrifuge. In some embodiments, a cooling system and a heating system are comprised in a singular embodiment such that one system both cools and heats the saliva sample. Additionally, in some embodiments, the rotation of the centrifuge generates energy that is harnessed for use in the cooling system, heating system, or any combination thereof.

A centrifuge puts the saliva sample in rotation around a fixed axis by applying a force perpendicular to the fixed axis. The rotation is actuated by an electric motor or the like. An electric motor converts electric current into mechanical rotation. Additionally, an electric motor provides for different angular velocities to be utilized with the use of a control system. A centrifuge operates using the sedimentation principle, wherein the centripetal acceleration forces denser substances to separate out along the radial direction and lighter objects tend to move in the opposite direction. Accordingly, the sample is housed in a tube like structure such that denser objects move to the bottom of the structure and the lighter objects move to the top of the structure. In saliva filtering, a centrifuge facilitates the process of separating unwanted particulates from desired saliva, wherein the particulates settle to the bottom of the tube like structure and the desired saliva rises to the top of the structure. Optionally, the tube like structure is fixed at an angle to facilitate easier movement of particulates within the sample.

In some embodiments, the thermal-centrifugal filter is miniaturized to allow for use with small samples of saliva. In a miniaturized thermal-centrifugal filter, the cooling system is sized and optimized to cool smaller saliva samples in a shorter amount of time. Additionally, the heating system and the cooling system are comprised in a singular embodiment such that one condition of the singular embodiment provides cooling and another condition of the singular embodiment provides heating. Further still, the centrifuge is miniaturized with the utilization of an optimized electric motor for the smaller saliva sample being filtered. Moreover, the tube like structure is sized for use with the smaller saliva sample.

In some embodiments, the thermal-centrifugal filter is contained in a singular system such that the cooling system, heating system, and centrifuge are all contained within an enclosed system. In some embodiments, the singular system thermal-centrifugal filter is sized to be readily operable on a tabletop in a consumer or laboratory setting. In some embodiments, the singular system thermal-centrifugal filter comprises automated steps, wherein the collected sample is transferred to the tube like structure of the centrifuge and frozen, thawed, and centrifuged without human interaction. Additionally, the singular system thermal-centrifugal filter is automated in the extraction of the desired saliva sample such that the desired saliva sample is extracted from the tube like structure and readied for evaluation without human interaction.

In some embodiments, the filter system is at least one membrane filter configured to block certain size particles. A membrane filter comprises an array of holes that allow particles to pass through that are smaller than a specified size. Consequently, the holes do not allow particles to pass through that are larger than the specified size, thus blocking the larger particles and effectively filtering the particles. Optionally, multiple membrane filters comprise the filter system, wherein each membrane filter is optimized to filter out a certain size particle such that passage through the multiple membrane filters effectively filters all sizes of unwanted particles.

In some embodiments, an evaluation system is configured to evaluate at least one saliva sample transferred from the collection system or filter system of the salivary diagnostic system for the detection and diagnosis of disease. In general, the evaluation system evaluates at least one saliva sample and provides a reportable assessment of the saliva sample in relation to the diagnosis and detection of disease and disease risk characteristics. A plurality of tests exists for the evaluation of saliva to diagnose and detect disease and disease risk characteristics. Common evaluation techniques are chosen from the group enzyme-linked immunosorbent assay (ELISA), polymerase chain reaction (PCR), high-resolution mass spectrometry (HRMS), heavy metal detection, fiber-optic-based detection, and any combination thereof. Accordingly, a plurality of diseases and conditions is detected and diagnosed using these common evaluation techniques. Some of these diseases and conditions are chosen from the group reproductive hormone irregularities, pancreatic cancer, breast cancer, oral cancer, human immunodeficiency virus, viral hepatitis, parasitic infection, *Helicobacter pylori* infection, periodontal disease, influenza, cardiovascular disease, dental caries, use of illicit drugs, and other cancers. Moreover, further diseases and conditions are being detected and diagnosed through saliva diagnostics.

Accordingly, the evaluation system provides a standardized system to perform a plurality of saliva tests using the saliva sample collected by the collection system and, often, filtered by the filter system. In the present invention, the evaluation system provides a platform for a plurality of saliva diagnostic tests such that the plurality of saliva diagnostic tests is performed by a singular evaluation system. The present invention of the evaluation system provides a standardized platform that allows for easy integration of saliva diagnostic tests.

In some embodiments, the evaluation system is a cartridge evaluation system comprising a console that is configured to couple to at least one cartridge for evaluation of a saliva sample, wherein a cartridge is configured to perform at least one saliva diagnostic test. Optionally, the saliva sample is transferred to the console from the collection system or filter system. The console is configured to couple to at least one cartridge, wherein a cartridge is retained by and fluidly coupled to the console. In operation, the console fluidly transfers the saliva sample to a cartridge where a saliva diagnostic test is performed by the cartridge in conjunction with the console. The console provides the necessary utilities to the cartridge to effectively perform the saliva diagnostic test. Additionally, the console is configured to determine the outcome of the test performed by the cartridge. In the case of test outcome being determined by a color change, the console comprises an optical sensor that determines outcome of the test. Accordingly, the console is configured to determine the outcome of the various saliva diagnostic tests conducted by the cartridges.

In some embodiments, a cartridge of the cartridge evaluation system is disposable, wherein a cartridge is a single-use product and is disposed after use. Optionally, a cartridge is arranged to be electronically coupled to the console such that the cartridge and the console are in analog and/or digital communication. The electronic coupling of the cartridge and the console provides for communication chosen from the group identification of the test the cartridge performs, progress of testing, results of testing, saliva sample data, and any combination thereof.

In some embodiments, the evaluation system comprises at least one data transfer medium plug-in system, wherein the evaluation system is configured to be a plug-in to a data transfer medium, such as the data transfer medium of the connected health care system, such that the plug-in utilizes the computing power of the data transfer medium and data is communicated between the two. Optionally, the plug-in operates in the same manner as the cartridge evaluation system described above but utilizes the computing power and convenience of the mobile communication device. Accordingly, a different cartridge is used for different tests and plug-in in conjunction with the mobile communication device acts as the console. In the present invention, the features of the mobile communication device are utilized for the evaluation of the saliva sample.

Alternatively, the plug-in comprises all of the necessary components to complete a certain saliva diagnostic test, wherein a separate plug-in is used for each saliva diagnostic test. Accordingly, the plug-in is removed from the mobile communication device after a test is completed and replaced with a different plug-in to conduct a different test.

In some embodiments, the evaluation system comprises a plurality of specified tests that are built into the system such that the utilities necessary to complete a plurality of tests are comprised in the evaluation system. Accordingly, the present embodiment does not require the use of interchangeable and/or disposable cartridges to perform different tests. Optionally, the evaluation system is partitioned such that different tests are performed within the same system. Additionally, the evaluation system is partitioned in such a way that multiple tests are performed concurrently. Accordingly, the saliva sample is transferred from the collection system or filter system and the evaluation system performs specified saliva diagnostic tests without human interaction, thus providing an automated evaluation system.

In some embodiments, the evaluation system is external to the other systems that comprise the saliva diagnostic system. Accordingly, the saliva sample is received from the collection system or filter system and transferred to the evaluation system using human interaction. The test is conducted by the evaluation system at different site from the collection and/or filtering of the saliva sample. For example, the saliva sample is collected and filtered in the home of the patient, and it is delivered to a laboratory where it is evaluated.

In some embodiments, the evaluation system comprises a transmitter that transmits results of tests performed by the evaluation system. The transmitter is chosen from the group universal serial bus (USB), serial port, wired Ethernet port, radio frequency, microwave communication, infrared short-range communication, near field communication, and Bluetooth.

In some embodiments, at least one of the systems chosen from the group collection system, filter system, evaluation system, and any combination thereof is comprised in a toothbrush. Optionally, the toothbrush comprises a collection system such that the user collects the saliva sample with the toothbrush used daily. Alternatively, the toothbrush comprises both a collection system and a filter system, wherein the user's toothbrush collects a saliva sample and filters said saliva sample such that the saliva sample is readied for evaluation within the toothbrush. In the toothbrush comprising a collection system and a filter system, the toothbrush is fluidly coupled to an evaluation system to transfer the saliva sample. Alternatively, the toothbrush comprises and risk characteristics of disease.

In some embodiments, at least one of the systems chosen from the group collection system, filter system, evaluation system, and any combination thereof is comprised in a data transfer medium plug-in. Optionally, the data transfer medium plug-in comprises a collection system, a filter system, and an evaluation system, wherein the mobile device plug-in collects a saliva sample, filters said saliva sample, and evaluates the saliva sample for the diagnosis and detection of disease and risk characteristics of disease with the aid of the data transfer medium.

In some embodiments, at least one of the systems chosen from the group collection system, filter system, evaluation system, and any combination thereof is comprised in a stand-alone system. Accordingly, the stand-alone system is only used for the purpose of saliva diagnostic testing. Optionally, the stand-alone system comprises a collection system, wherein the stand-alone system is used to collect a saliva sample. Alternatively, the stand-alone system comprises both a collection system and a filter system, wherein the stand-alone system collects a saliva sample and filters said saliva sample. Alternatively, the stand-alone system comprises a collection system, a filter system, and an evaluation system, wherein the stand-alone system collects a saliva sample, filters said saliva sample, and evaluates the saliva sample for the diagnosis and detection of disease and risk characteristics of disease.

In some embodiments, a reporting system is configured to report the results of the saliva diagnostic tests performed by an evaluation system. In general, the reporting system reports, processes, and stores the results of testing performed by the evaluation system. The reporting system utilizes the data transfer medium and the Cloud of the connected health care system to effectively process, store, and report results of test completed by the evaluation system.

In some embodiments, the collection system, the filter system, the evaluation system, the reporting system, and any combination thereof is comprised in the user identification system as either the mobile unit or the base unit. Optionally, the mobile unit is the toothbrush or data transfer medium of the connected health care system, wherein each system of the salivary diagnostic systems is a base unit.

In some embodiments, the connected health care system further comprises a breath analysis system that diagnoses and monitors disease characteristics such as diabetes mellitus. The breath analysis system is comprised as a handheld device with an interchangeable mouthpiece such that different mouthpieces can be used by different users or the mouthpiece is disposable. Optionally, the breath analysis system is constructed such that it can be detachably connected to the toothbrush handle of the toothbrush previously described herein when the toothbrush head is disconnected.

The breath analysis system further comprises a data processing unit having at least one collector, a storage medium, and at least one processor, wherein the collector, storage medium, and processor, respectively, collect, store, and process data. Accordingly, the data processing unit is chosen from the group microprocessor, microcontroller, field programmable gate array (FPGA), digital signal processing unit (DSP), application specific integrated circuit (ASIC), programmable logic, and combinations thereof.

Additionally, in some embodiments, the collector of the data processing unit is an electrically conductive wire, wherein the electrically conductive wire receives the electrical output of various sensors.

Moreover, the storage medium of the data processing unit is comprised of volatile memory and non-volatile memory, wherein volatile memory is used for short-term storage and processing, and non-volatile memory is used for long-term storage. Accordingly, volatile memory is chosen from the group random-access memory (RAM), dynamic random-access memory (DRAM), double data rate synchronous dynamic random-access memory (DDR SDRAM), static random-access memory (SRAM), thyristor random-access memory (T-RAM), zero-capacitor random-access memory (Z-RAM), and twin transistor random-access memory (TTRAM). Non-volatile memory is chosen from the group read-only memory (ROM), programmable read-only memory (PROM), erasable programmable read-only memory (EPROM), electrically erasable programmable read-only memory (EEPROM), flash memory, ferroelectric random-access memory (FeRAM), magnetoresistive random-access memory (MRAM), phase-change memory (PRAM), conductive-bridging random-access memory (CBRAM), silicon-oxide-nitride-oxide-silicon memory (SONOS), resistive random-access memory (RRAM), racetrack memory, nano-random-access memory (NRAM), and Millipede memory.

The processor of the data processing unit is chosen from the group microprocessor and micro controller.

Optionally, the breath analysis system further comprises at least one data transmitter, such that the data can be transmitted to be used by another medium. The data is packaged as at least one signal and transmitted to another medium. The data transmitter is chosen form the group universal serial bus (USB), serial port, wired Ethernet port, radio frequency, microwave communication, infrared short-range communication, near field communication, and Bluetooth®.

In some embodiments, the breath analysis system further comprises at least one semiconducting oxide gas sensor, wherein the resistance of the semiconducting oxide is varied by the presence of certain gases. Optionally, a semiconducting oxide gas sensor detects the presence of acetone such that the electrical resistance is lowered as the amount of acetone increases. The presence of acetone in the breath increases significantly during periods of glucose deficiency, which is an indicator of diabetes. Accordingly, an increased presence of acetone in the breath that is detected by the semiconducting oxide gas sensor is indicative of the disease diabetes mellitus.

Additionally, the semiconducting oxide gas sensor has sensitivity as to detect a specific amount of acetone in the breath of the user. The measured acetone level is transmitted to the data processing unit of the breath analysis system. Optionally, the data processing unit of the breath analysis system processes the acetone level data in correlation with standardized acetone-to-glucose data such that a glucose level is determined from the measurement of the semiconducting oxide gas sensor. Conversely, the measured acetone level data is transmitted from the breath analysis system via the data transmitter to a data transfer medium and/or the Cloud where it is further processed to obtain a glucose level from the semiconducting oxide gas sensor.

In some embodiments, the breath analysis system is comprised in a user identification system such that the breath analysis system is a mobile unit in the user identification system. Optionally, the breath analysis system identifies the user to the connected surface that acts as the base unit using capacitive coupling of the human body.

Optionally, the interchangeable mouthpiece of the breath analysis system is used to identify individual users to the breath analysis system. Furthermore, identification of the user by the interchangeable mouthpiece acts to provide identification to the mobile unit of the user identification system that allows multiple users to use the same data processing unit for the mobile unit.

In some embodiments, the connected health care system facilitates the user's participation in social games related to the data collected by the devices of the connected health care system. Participation in said social games is accomplished passively through the collection of data by the devices of the connected health care system over a period of time, rather than participation by real-time user input. Optionally, the social games consist of goals to be accomplished, competitive games between multiple users or between a singular user and a computer generated user, and challenges to complete specified milestones.

Participation in social games is accomplished through a plurality of different user groups. The first user group for participation is a closed loop user group, which is accomplished on a specific data transfer medium and participation is limited to the users of said specific data transfer medium. The second user group for participation is a networked user group, which is accomplished over a network that connects a plurality of data transfer mediums. Networked user groups are further defined as including users belonging to a certain group defined through social media or other means. The third user group for participation is a global user group, which is a user group that anyone can join and participate in. The global user group, in some embodiments, may be sponsored or promoted by a particular entity as a form of advertisement or incentive to the users of the global user group.

Participation in social games may be incentivized with an offered reward to encourage participation of members of a user group. Rewards may include coupons, discounts on goods or services, virtual currency, insurance discounts, and customized incentives. Rewards have the advantage of being given based off of passive data collected by sensors, thus rewarding users for health compliance and health statistics.

In some embodiments, the connected health care system facilitates the development of user health ratings that affect insurance underwriting, health procedure determination, health outcomes, provider offered services, health care costs, and any combination thereof based on the data provided by the devices of the connected health care system. The data collected by the devices of the connected health care system is transmitted to a data transfer medium and/or the Cloud by the various data transmitters in conjunction with the respective data processing units. The data collected by devices of the connected health care system is processed and stored by the Cloud such that user health ratings are created in various health categories including oral health, heart health, fitness, and others. The user health ratings are created by the data processing unit of the Cloud with consideration given to the data from the devices of the connected health care system.

Optionally, the user health ratings are factored into health and dental insurance underwriting of policies such that more favorable user health ratings are indicative of lower insurance premiums and more favorable coverage. Additionally, the user health ratings are factored in to determinations of services offered to the user by a health care provider such that the user health rating helps determine the proper treatment for a certain affliction or offerings of preventative treatments. Furthermore, the user health ratings are utilized to provide better health outcomes to the user from the service provider by offering preventative and specialized treatment based on the user health ratings.

It will be understood that the embodiments described herein are not limited in their application to the details of the teachings and descriptions set forth, or as illustrated in the accompanying figures. Rather, it will be understood that the connected health care system, as taught and described according to multiple embodiments disclosed herein, is capable of other embodiments and of being practiced or carried out in various ways.

Also, it is to be understood that the phraseology and terminology used herein is for the purpose of description and should not be regarded as limiting. The use herein of "including," "comprising," "i.e.," "containing," or "having," and variations of those words is meant to encompass the items listed thereafter, and equivalents of those, as well as additional items.

Accordingly, the descriptions herein are not intended to be exhaustive, nor are they meant to limit the understanding of the embodiments to the precise forms disclosed. It will be understood by those having ordinary skill in the art that modifications and variations of these embodiments are reasonably possible in light of the above teachings and descriptions.

What is claimed is:

1. A connected health care system for monitoring one or more health statistics of a user, the connected health care system comprising:
   a cloud computing network having at least one data processing unit that stores and processes data and a transceiver that receives and transmits data;
   a connected surface having a contact surface that allows the user to stand thereon during normal daily activities, a data processing unit that stores and processes data, a transceiver that receives and transmits data, a weight sensor that measures weight and balance, and a power source; and
   a connected implement having a handle, a data processing unit, a transceiver, a power source, and a salivary diagnostics system, the salivary diagnostics system further comprising:
      a collection system that collects at least one saliva sample from the user,
      a thermal-centrifugal filter system that treats the at least one saliva sample, where the collection system is detachably coupled to the thermal-centrifugal filter system, and
      an evaluation system that analyzes the at least one saliva sample to detect and/or diagnose a disease or a disease risk characteristic, the thermal-centrifugal filter system and the evaluation system being enclosed within a single unit.

2. The connected health care system of claim 1, further comprising a data transfer medium having a transceiver that receives and transmits data, a data processing unit that stores and processes data, and a display medium that displays data.

3. The connected health care system of claim 1, wherein the connected health implement is a toothbrush that comprises a plurality of bristles, a pressure sensor that detects brushing pressure, and an orientation sensor that detects a position of the toothbrush.

4. The connected health care system of claim 1, wherein the connected surface further comprises at least one additional sensor selected from the group consisting of an oximetry sensor, an ultrasonic sensor that measures bone density, a thermal imaging sensor, a galvanic skin response sensor, a body fat sensor, an electrocardiogram sensor that measures the rate and regularity of heartbeats, a pressure point sensor that identifies pressure points, and a temperature sensor, and any combination thereof.

5. The connected health care system of claim 1, wherein the connected health implement is a breath analysis system having a mouthpiece and a semiconducting oxide gas sensor that detects amounts of acetone in breath.

6. The connected health care system of claim 1, further comprising a user identification system having at least one mobile unit, at least one base unit, and a capacitive coupler that connects the mobile unit to the the base unit such that the mobile unit communicates with the base unit.

7. The connected health care system of claim 6, wherein the mobile unit is selected from the group consisting of a toothbrush, the collection system, the thermal-centrifugal filter system, the evaluation system, the reporting system, a data transfer medium, a data transfer medium plug-in, a breath analysis system, and a breath analysis system interchangeable mouthpiece, and any combination thereof.

8. The connected health care system of claim 6, wherein the base unit is selected from the group consisting of the connected surface, a data transfer medium, a data transfer medium plug-in, the collection system, the thermal-centrifugal filter system, the evaluation system, the reporting system, and a breath analysis system, and any combination thereof.

9. A connected health care system for monitoring one or more health statistics of a user, the connected health care system comprising:
- a cloud computing network having at least one data processing unit that stores and processes data and a transceiver that receives and transmits data;
- a connected implement having a handle, a data processing unit that stores and processes data, a transceiver that receives and transmits data, a power source, and a salivary diagnostics system, the salivary diagnostics system further comprising:
  - a collection system that collects at least one saliva sample from the user,
  - a thermal-centrifugal filter system that treats the at least one saliva sample, where the collection system is detachably coupled to the thermal-centrifugal filter system, and
  - an evaluation system that analyzes the at least one saliva sample to detect and/or diagnose a disease or a disease risk characteristic, the thermal-centrifugal filter system and the evaluation system being enclosed within a single unit;
- a connected surface having a contact surface that allows the user to stand thereon during normal daily activities, a data processing unit that stores and processes data, a transceiver that receives and transmits data, a weight sensor that measures weight and balance, and a power source; and
- a data transfer medium having a transceiver that receives and transmits data, a data processing unit that stores and processes data, a display medium that displays data, and a user interface that facilitates participation in social games such that participation is accomplished passively through data collection of the connected implement and the connected surface over a period of time.

10. The connected health care system of claim 9, wherein the connected implement is a toothbrush that comprises a plurality of bristles, a pressure sensor that detects excessive brushing pressure, and an orientation sensor that detects the position of the toothbrush.

11. The connected health care system of claim 9, wherein the connected surface further comprises at least one sensor selected from the group consisting of an oximetry sensor, an ultrasonic sensor that measures bone density, a thermal imaging sensor, a galvanic skin response sensor, a body fat sensor, an electrocardiogram sensor that measures the rate and regularity of heartbeats, a pressure point sensor that identifies pressure points, and a temperature sensor, and any combination thereof.

12. The connected health care system of claim 9, wherein the connected implement is a breath analysis system that comprises a mouthpiece and a semiconducting oxide gas sensor that detects amounts of acetone in breath.

13. The connected health care system of claim 9, further comprising a user identification system having at least one mobile unit, at least one base unit, and a capacitive coupler that connects the mobile unit to the the base unit such that the mobile unit communicates with the base unit.

14. The connected health care system of claim 13, wherein the mobile unit is selected from the group consisting of a toothbrush, the collection system, the thermal-centrifugal filter system, the evaluation system, the reporting system, a data transfer medium, a data transfer medium plug-in, a breath analysis system, and a breath analysis system interchangeable mouthpiece, and any combination thereof.

15. The connected health care system of claim 13, wherein the base unit is selected from the group consisting of the connected surface, the data transfer medium, a data transfer medium plug-in, the collection system, the thermal-centrifugal filter system, the evaluation system, the reporting system, and a breath analysis system, and any combination thereof.

16. A connected health care system for monitoring one or more health statistics of a user, the connected health care system comprising:
- a connected implement having a handle, a data processing unit that stores and processes data, a transceiver that receives and transmits data, a power source, and a salivary diagnostics system, the salivary diagnostics system comprising:
  - a collection system that collects at least one saliva sample from the user,
  - a thermal-centrifugal filter system that treats the at least one saliva sample, where the collection system is detachably coupled to the thermal-centrifugal filter system, and
  - an evaluation system that analyzes the at least one saliva sample to detect and/or diagnose a disease or a disease risk characteristic, the thermal-centrifugal filter system and the evaluation system being enclosed within a single unit;
- a connected surface having a surface that allows the user to stand thereon during normal daily activities, a data processing unit that stores and processes data, a transceiver that receives and transmits data, a weight sensor that measures weight and balance, and a power source; and
- a cloud computing network having at least one data processing unit that stores and processes data and a transceiver that receives and transmits data, wherein the cloud computing network creates user health ratings that affect at least one decision selected from the group consisting of insurance underwriting, risk modeling, diagnostic decisions, health procedure determination, health outcomes, provider offered services, access to a health benefit, access to an insurance product, health care costs, and health benefit incentives, and any combination thereof.

17. The connected health care system of claim 16, wherein the connected implement is a toothbrush that comprises a plurality of bristles, a pressure sensor that detects excessive brushing pressure, and an orientation sensor that detects the position of the toothbrush.

18. The connected health care system of claim 16, wherein the connected surface further comprises at least one additional sensor that is selected from the group consisting of an oximetry sensor, an ultrasonic sensor that measures bone density, a thermal imaging sensor, a galvanic skin response sensor, a body fat sensor, an electrocardiogram sensor that measures the rate and regularity of heartbeats, a pressure point sensor that identifies pressure points, and a temperature sensor, and any combination thereof.

19. The connected health care system of claim 9, wherein participation in the social games is accomplished through a plurality of user groups.

20. The connected health care system of claim 19, wherein the user groups are selected from the group consisting of a networked user group that is accomplished over a network that connects a plurality of remote data transfer mediums, a global user group, and a closed loop user group, and any combination thereof.

\* \* \* \* \*